US009114086B2

(12) United States Patent
Hsia et al.

(10) Patent No.: US 9,114,086 B2
(45) Date of Patent: Aug. 25, 2015

(54) COATED TABLETS OF ESZOPICLONE (71) Applicant: Sunovion Pharmaceuticals Inc., Marlborough, MA (US)

(72) Inventors: Richard Hsia, Boston, MA (US); Cai Gu Huang, Sudbury, MA (US); Konstantinos E. Saranteas, Peabody, MA (US); Tushar K. Misra, Norfolk, MA (US); Philip J. Bonasia, Jr., Needham, MA (US)

(73) Assignee: Sunovion Pharmaceuticals Inc., Malborough, MA (US)

( * ) Notice: Subject to any disclaimer, the term of this patent is extended or adjusted under 35 U.S.C. 154(b) by 0 days.

(21) Appl. No.: 14/243,146

(22) Filed: Apr. 2, 2014

(65) Prior Publication Data
US 2014/0271858 A1    Sep. 18, 2014

Related U.S. Application Data (63) Continuation of application No. 12/695,701, filed on Jan. 28, 2010, now abandoned.

(60) Provisional application No. 61/148,621, filed on Jan. 30, 2009.

(51) Int. Cl.
*A61K 9/20* (2006.01)
*A61K 9/30* (2006.01)
*A61K 31/4985* (2006.01)
*A61K 9/28* (2006.01)

(52) U.S. Cl.
CPC ............ *A61K 9/2866* (2013.01); *A61K 31/4985* (2013.01); *Y10T 436/147777* (2015.01)

(58) Field of Classification Search
CPC ............ A61K 31/495; A61K 31/4965; A61K 31/4985; A61K 9/20; A61K 9/2068; A61K 9/5063; A61K 9/2806; A61K 9/2866; C07D 471/00; C07D 495/00
See application file for complete search history.

(56) References Cited

U.S. PATENT DOCUMENTS

| 4,543,370 | A | 9/1985 | Porter et al. |
| 5,098,715 | A | 3/1992 | McCabe et al. |
| 5,733,575 | A | 3/1998 | Mehra et al. |
| 6,309,668 | B1 | 10/2001 | Bastin et al. |
| 6,451,345 | B1 | 9/2002 | Percel et al. |

(Continued)

FOREIGN PATENT DOCUMENTS

| WO | WO 2005/079851 | 9/2005 |
| WO | WO 2005/097132 | 10/2005 |

(Continued)

OTHER PUBLICATIONS

International Search Report dated Jul. 22, 2010 for related International Patent Application No. PCT/US2010/022402.

(Continued)

*Primary Examiner* — Lakshmi Channavajjala
(74) *Attorney, Agent, or Firm* — Heslin, Rothenberg, Farley & Mesiti, P.C.

(57) ABSTRACT

Coated tablets of (6-(5-chloro-2-pyridyl)-5-[(4-methyl-1-piperazinyl)carbonyloxy]-7-oxo-6,7-dihydro-5H-pyrrolo[3,4-b]pyrazine) are provided. The tablets minimize the perceived bitterness of the medicament. A method for analyzing instantaneous dissolution of sub-microgram quantities of core material is also disclosed.

6 Claims, 3 Drawing Sheets

(56) References Cited

U.S. PATENT DOCUMENTS

| | | | |
|---|---|---|---|
| 7,357,945 | B2 | 4/2008 | Cohen et al. |
| 7,476,737 | B2 | 1/2009 | Mandava et al. |
| 8,198,277 | B2* | 6/2012 | Wilkinson et al. ............ 514/249 |
| 8,198,278 | B2* | 6/2012 | Hsia et al. .................... 514/249 |
| 8,212,036 | B2* | 7/2012 | Wilkinson et al. ............ 544/350 |
| 8,268,832 | B2* | 9/2012 | Wilkinson et al. ....... 514/255.01 |
| 8,269,005 | B2* | 9/2012 | Wilkinson et al. ............ 544/350 |
| 8,497,267 | B2* | 7/2013 | Hsia et al. .................... 514/249 |
| 8,497,268 | B2* | 7/2013 | Wilkinson et al. ............ 514/249 |
| 8,541,416 | B2* | 9/2013 | Wilkinson et al. ............ 514/249 |
| 2007/0098788 | A1 | 5/2007 | Gore et al. |
| 2007/0207203 | A1 | 9/2007 | Cheng et al. |
| 2009/0269409 | A1 | 10/2009 | Garg et al. |

FOREIGN PATENT DOCUMENTS

| | | |
|---|---|---|
| WO | WO 2007/006003 | 1/2007 |
| WO | WO 2007/065625 | 6/2007 |

OTHER PUBLICATIONS

Gulian et al. "Taste Masking Performance and Stability of Opadry tm, a Taste Mask Film Coating System", Amer. Academy of Pharmaceutical Scientists, Nov. 2004.

"Effective Taste Masking Solutions from Colorcon", Colorcon, Inc., 2008.

Doshier et al. "Method Development Tools for the Analysis of Complex Pharmaceutical Samples", Amer. Laboratory, Dec. 2002, 19-23.

Archived drug label-cetrizine hydrochloride, Oct. 2009, 6 pages.

* cited by examiner

COATED TABLETS OF ESZOPICLONE

CROSS REFERENCE TO RELATED APPLICATIONS

This application is related to U.S. application Ser. Nos. 12/338,899, 12/338,903 and 12/338,908, all filed on Dec. 18, 2008, which are incorporated herein by reference in their entirety. This application is a continuation of U.S. application Ser. No. 12/695,701, which was filed Jan. 28, 2010. U.S. Ser. No. 12/695,701 claims priority to U.S. provisional application 61/148,621, filed Jan. 30, 2009, both of which are Incorporated herein by reference in their entirety.

FIELD OF THE INVENTION

The present invention relates to coated oral solid dosage forms and to methods for testing the effectiveness of the coating on said solid dose.

BACKGROUND OF THE INVENTION

Eszopiclone, also known as (S)-zopiclone or (S)-(6-(5-chloro-2-pyridyl)-5-[(4-methyl-1-piperazinyl)carbonyloxy]-7-oxo-6,7-dihydro-5H-pyrrolo[3,4-b]pyrazine), is formulated as the free base and is sold as LUNESTA®. It is used to treat different types of sleep problems, such as difficulty in falling asleep, difficulty in maintaining sleep during the night, and waking up too early in the morning. Most people with insomnia have more than one of these problems. See, e.g., WO 93/10787; Brun, J. P., Pharm. Biochem. Behav. 29: 831 832 (1988). The compound eszopiclone and various methods of treatment are disclosed at least in the following U.S. Pat. Nos. 7,125,874; 6,864,257; 6,444,673; 6,319,926; and 5,786,357.

Racemic zopiclone, rac-(6-(5-chloro-2-pyridyl)-5-[(4-methyl-1-piperazinyl)carbonyloxy]-7-oxo-6,7-dihydro-5H-pyrrolo[3,4-b]pyrazine), also formulated as the free base, has been sold in Europe for many years to treat different types of sleep problems.

The active ingredient eszopiclone in its free base form has a very strong bitter taste. Human taste studies indicated that even a solution with very low concentration, e.g., 0.01 mg/mL, the bitter taste can be detected by the human tongue. Therefore, trace amounts of the active ingredient on the surface of the tablets, or any film coating defects leading to the direct exposure of the active ingredient on the surface of the tablets, or instantaneous dissolving tablets in human mouths would be detected owing to the extremely bitter taste when the patients swallow LUNESTA® tablets with water.

Many forms of analytical methods and apparatus have been proposed to measure or identify the active ingredient on the surface of the tablets. For instance, Raman mapping spectra were used to detect the active ingredient of alprazolam from the flattened surfaces of six alprazolam tablets (Sasic, Slobodan. Analytical R&D, Pfizer Global Research and Development, Sandwich, UK). *Pharmaceutical Research* (2007), 24(1), 58-65). Additionally, many analytical methods have been proposed to evaluate the film coating property of tablets. For example, the novel X-ray photoelectron spectroscopic (XPS) technique combined with principal component analysis of spectra-to-image datasets was employed to study the effects of atomization air pressure used during the coating process on film-tablet interfacial thickness (Barbash, Dmytro; Fulghum, Julia E.; Yang, Jing; Felton, Linda. Physical Electronics USA, Inc., Chanhassen, Minn., USA, *Drug Development and Industrial Pharmacy* (2009), 35(4), 480-486.) But none of these techniques are able to accurately determine very small amounts of material at very short time frames.

Human taste panel studies, such as the "Lick and Roll" testing method (a method involving direct collection of human saliva from the patients who take LUNESTA® tablets) is not only time-consuming, but also requires large and expensive clinical studies. Further, the conventional dissolution method is not capable of capturing the dissolution profiles of the tablets in the incipient stages of dissolution because sampling requires time intervals of five minutes or longer. On the other hand, methods such as conventional UV fiber optics and/or LC-UV methods, while rapid, are not sensitive enough to accurately quantify the trace amount of the active pharmaceutical ingredient at the ng/mL level. Therefore, there is a strong need to develop a new method which can overcome the drawbacks of the known methods or techniques in the art.

SUMMARY OF THE INVENTION

In one aspect, the present invention provides a pharmaceutical composition for oral administration as a solid dose comprising a therapeutically effective amount of (6-(5-chloro-2-pyridyl)-5-[(4-methyl-1-piperazinyl)carbonyloxy]-7-oxo-6,7-dihydro-5H-pyrrolo[3,4-b]pyrazine) or (S)-(6-(5-chloro-2-pyridyl)-5-[(4-methyl-1-piperazinyl)carbonyloxy]-7-oxo-6,7-dihydro-5H-pyrrolo[3,4-b]pyrazine), or a salt thereof, coated with a water-soluble polymeric coating, said polymeric coating comprising about 2% to about 10% by weight of the composition.

In another aspect, the present invention provides a composition which is capable of masking the taste of (6-(5-chloro-2-pyridyl)-5-[(4-methyl-1-piperazinyl)carbonyloxy]-7-oxo-6,7-dihydro-5H-pyrrolo[3,4-b]pyrazine) or (S)-(6-(5-chloro-2-pyridyl)-5-[(4-methyl-1-piperazinyl)carbonyloxy]-7-oxo-6,7-dihydro-5H-pyrrolo[3,4-b]pyrazine), or a salt thereof.

In another aspect, the present invention provides a process for preparing a pharmaceutical composition comprising providing from 0.5 to 5 mg of (6-(5-chloro-2-pyridyl)-5-[(4-methyl-1-piperazinyl)carbonyloxy]-7-oxo-6,7-dihydro-5H-pyrrolo[3,4-b]pyrazine) or (S)-(6-(5-chloro-2-pyridyl)-5-[(4-methyl-1-piperazinyl)carbonyloxy]-7-oxo-6,7-dihydro-5H-pyrrolo[3,4-b]pyrazine) or a salt thereof in the from of a tablet; and spray-coating the tablet with an aqueous dispersion comprising a cellulose derivative to provide a coating comprising about 2% to about 10% by weight of the composition.

In another aspect, the invention relates to a method for determining the presence of exposed core material in a coated solid oral dosage form comprising a core and a coating. The method comprises the following steps: (a) providing ex vivo a dissolution medium; (b) bringing the coated solid oral dosage form into contact with the dissolution medium; and (c) measuring a concentration of the core material dissolved in the dissolution medium within 5 minutes, or even within 60 seconds, of bringing the coated solid oral dosage form into contact with the dissolution medium. The method uses liquid chromatography and tandem mass spectroscopy (LC-MS/MS). The method may be used to determine trace amounts of a core material on the surface of a coated solid oral dosage form, to detect film coating defects, or to predict unpleasant taste of film coated tablets.

The invention is also directed towards a method for treatment, prevention, or amelioration of a sleep disorder in a subject comprising administering to a subject in need thereof, a composition described above. The invention further includes a method for treatment, prevention, or amelioration of anxiety in a subject comprising administering to a subject in need thereof, a composition described above.

In one aspect, the invention provides a use of a composition described above in the manufacture of a medicament for the treatment, prevention or amelioration of a sleep disorder.

In another aspect, the invention provides a use of a composition described above in the manufacture of a medicament for the treatment, prevention or amelioration of anxiety.

DETAILED DESCRIPTION OF THE INVENTION

In one aspect, the invention provides a pharmaceutical composition for oral administration as a solid dose comprising a therapeutically effective amount of (6-(5-chloro-2-pyridyl)-5-[(4-methyl-1-piperazinyl)carbonyloxy]-7-oxo-6,7-dihydro-5H-pyrrolo[3,4-b]pyrazine) or (S)-(6-(5-chloro-2-pyridyl)-5-[(4-methyl-1-piperazinyl)carbonyloxy]-7-oxo-6,7-dihydro-5H-pyrrolo[3,4-b]pyrazine), or a salt thereof, coated with a water-soluble polymeric coating, the polymeric coating comprising about 2% to about 10% by weight of the composition. In some embodiments, the coating comprises an amount between about 3% to about 8% by weight of the composition, or preferably an amount between about 4% to about 7% by weight of the composition, or more preferably an amount between about 4% to about 6% by weight of the composition.

In some embodiments, the invention provides a pharmaceutical composition as described above wherein the coating comprises at least one cellulose derivative. The cellulose derivative can be selected from the group consisting of a cellulose ether and a cellulose ester. In some embodiments, the coating comprises at least one of hydroxypropyl methylcellulose, hydroxypropyl cellulose, methyl cellulose, hydroxyethyl cellulose or mixtures thereof.

In some embodiments of the invention, the coating comprises Opadry® tm (Colorcon, West Point, Pa.). In yet other embodiments, the invention provides that the coating comprises at least one taste modifying agent. Other exemplary coatings include Opadry® II in conjunction with Opadry® Clear (Colorcon, West Point, Pa.).

In a preferred embodiment, the solid dose is a tablet.

In some embodiments, the composition is capable of masking the taste of (6-(5-chloro-2-pyridyl)-5-[(4-methyl-1-piperazinyl)carbonyloxy]-7-oxo-6,7-dihydro-5H-pyrrolo[3,4-b]pyrazine) or (S)-(6-(5-chloro-2-pyridyl)-5-[(4-methyl-1-piperazinyl)carbonyloxy]-7-oxo-6,7-dihydro-5H-pyrrolo[3,4-b]pyrazine), or a salt thereof, for at least about 10 seconds, or preferably at least about 20 seconds, or more preferably at least about 30 seconds. In some embodiments, the invention provides a composition capable of masking the taste of eszopiclone for about 20 seconds, or for about 30 seconds, or for about 45 seconds.

In some aspects of the invention, the coating comprises at least a cellulose ether, an emulsifier and a plasticizer. Plasticizers can be added to the coating formulations to modify the physical properties. For example a plasticizer can be used to modify the glass transition temperature (Tg) of the polymer to make it more usable. The Tg is the temperature at which an amorphous polymer (or the amorphous regions in a partially crystalline polymer) changes from a hard and relatively brittle condition to a viscous or rubbery condition. Plasticizers function by decreasing the Tg of the polymer so that under ambient conditions the films are softer, more pliable and often stronger, and thus better able to resist mechanical stress. Non-limiting examples of plasticizers include polyethylene glycol having a molecular weight of 200 to 8000, glycerin, propylene glycol, glycerin triacetate, acetylated monoglyceride, triethylcitrate, tributylcitrate, acetyltrithylcitrate, acetyltributylcitrate, diethyl phthalate, and mineral oil. An emulsifier, or emulsifying agent, can be used to facilitate actual emulsification during manufacture of the coat, and also to ensure emulsion stability during the shelf-life of the product. For example, naturally occurring materials and their semi synthetic derivatives, such as the polysaccharides, as well as glycerol esters, cellulose ethers, sorbitan esters and polysorbates can be used as emulsifiers. Non-limiting examples of emulsifiers that can be used in the present invention include polysorbate, polyethylene (20) sorbitan monooleate, Tween 80, and sodium lauryl sulfate. One or more emulsifiers can be present in an amount up to about 2% by weight of the coat composition and preferably from about 0.1% to about 0.5% by weight of the coat composition. Any of the pigments heretofore used in making coating dispersions for coating tablets and the like can be incorporated in the coating. Examples are FD&C and D&C lakes, titanium dioxide, magnesium carbonate, talc, pyrogenic silica, iron oxides, channel black, and insoluble dyes. Also natural pigments such as riboflavin, carmine 40, curcumin, and annatto. In some embodiments, the invention provides that the coating comprises about 5-25% titanium dioxide, about 25-70% hydroxypropyl methylcellulose, about 0-10% polyethylene glycol and about 0-2% polysorbate, respective weight to weight. In other embodiments, the invention provides that the coating comprises about 10-20% titanium dioxide, about 50-70% hydroxypropyl methylcellulose, about 0-5% polyethylene glycol and about 0-1% polysorbate, respective weight to weight.

In preferred embodiments, the coating is an immediate release coating. In other embodiments, enteric coatings, and coatings for modifying the rate of release can be used. For example, such coatings can comprise hydroxypropyl methylcellulose, sodium carboxymethylcellulose, cellulose acetate, cellulose acetate phthalate, ethylcellulose, gelatin, pharmaceutical glaze, hydroxypropyl cellulose, hydroxypropyl methyl cellulose phthalate, methacrylic acid copolymer, methylcellulose, polyethylene glycol, polyvinyl acetate phthalate, shellac, sucrose, titanium dioxide, wax, or zein. The coating material can further comprise anti-adhesives, such as talc; plasticizers (depending on the type of coating material selected), such as polyethylene glycol, castor oil, diacetylated monoglycerides, dibutyl sebacate, diethyl phthalate, glycerin, propylene glycol, triacetin, triethyl citrate; opacifiers, such as titanium dioxide; and/or coloring agents and/or pigments.

The coating can include one or more materials suitable for the regulation of release or for the protection of the formulation. In one embodiment, coatings are provided to permit either pH-dependent or pH-independent release, e.g., when exposed to gastrointestinal fluid. In some embodiments, multiple active agents can be formulated into a single unit dosage form. For example, a pH-dependent coating serves to release the first active agent, second active agent, or both in the desired areas of the gastrointestinal (GI) tract, e.g., the stomach or small intestine, such that an absorption profile is provided which is capable of providing at least about twelve hours and preferably up to twenty-four hours of therapeutic benefit to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine. In certain embodiments, the first therapeutic agent is released in one area of the GI tract and the second therapeutic agent is released in a second area of the GI tract. In certain embodiments, the first and second therapeutic agents are released in nearly equal amounts at the same location in the GI tract.

In addition to the above ingredients, a coating can also contain suitable quantities of other materials, e.g. diluents, lubricants, binders, granulating aids, colorants, taste modifying agents and glidants that are conventional in the pharmaceutical art.

In other aspects of the invention, the coating comprises at least one "taste modifying agent." As used herein, the term "taste modifying agent" is intended to refer to an agent capable of masking and/or changing the taste of the active ingredient. For example, taste modifying agents can include one or more sweetening agents, flavoring agents and/or cooling agents. The sweetening agent can be a sugar or may be a sugar substitute or mixtures thereof. Useful sweeteners include, but are not limited to, sugars such as sucrose, glucose (corn syrup), dextrose, invert sugar, fructose, and mixtures thereof; saccharin and its various salts such as the sodium or calcium salt; cyclamic acid and its various salts such as the sodium salt; the dipeptide sweeteners such as aspartame, alitame, neotame; sucralose, natural sweeteners such as dihydrochalcone compounds; glycyrrhizin; Stevia rebaudiana (Stevioside); sugar alcohols such as sorbitol, sorbitol syrup, mannitol, xylitol and the like, synthetic sweeteners such as acesulfame-K and sodium and calcium salts thereof and the like, hydrogenated starch hydrolysate (lycasin); protein based sweetening agents such as talin (thaumaoccous danielli) and/or any other pharmacologically acceptable sweetener known by the state of the art, and mixtures thereof.

The flavoring agents that can be used include those known to the skilled artisan, such as natural and artificial flavoring agents. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, wintergreen, eucalyptus clove oil, bay oil, thyme oil, cedar leaf oil, oil of nutmeg, oil of sage, and oil of bitter almonds. Also useful are artificial, natural or synthetic flavors such as vanilla, chocolate, coffee, cocoa and citrus oil, including lemon, orange, grape, lime and grapefruit and fruit essences including apple, pear, peach, strawberry, raspberry, cherry, plum, pineapple, apricot and so forth, flavoring agents such as eucalyptol, thymol, camphor, methyl salicylate, benzaldehyde, ginger and the like, acidulants such as citric acid, malic acid and the like. Flavorings such as aldehydes and esters including cinnamyl acetate, cinnamaldehyde, citral, diethylacetal, dihydrocarvyl acetate, eugenyl formate, p-methylanisole, and so forth may also be used. Agents which can provide a sensation of heat may also be used. These include but are not limited to capsicum, capsaicinoids, pipperine, gingerols, isothiocyanates, and materials such as chili pepper, horseradish, ginger, black pepper and the like. Generally, any flavoring or food additive, such as those described in Chemicals Used in Food Processing, publication 1274 by the National Academy of Sciences, pages 63-258, may be used. These flavorings can be used individually or in admixture.

Agents known as cooling agents include, but are not limited to, menthol, substituted p-menthanes, e.g., hydroxymethyl and hydroxyethyl derivatives, menthyl succinate (PHYSCOOL), menthyl lactates (e.g. FRESCOLAT), N,N-dimethyl menthyl succinamide; substituted-p-menthane-3-carboxamides, such as N-ethyl-p-menthane-3-carboximide (WS-3), N,2,3-trimethyl-2-isopropyl butamide (WS-23); acyclic carboxamides, substituted cyclohexanamides, substituted cyclohexane carboxamides, substituted ureas and sulphonamides, and substituted menthanols; 3-1-menthoxy propan-1,2-diol, menthoxypropane diol, menthone glycerol ketals, p-menthane-3,8-diols, 2-mercapto-cyclo-decanone, 2-isopropanyl-5-methylcyclohexanol (ISOPREGOL); isopulegol, cubebol, incilin, xylitol and others compounds known for their cooling effects and mixtures thereof.

As used herein, the terms zopiclone, 6-(5-chloro-2-pyridyl)-5-[(4-methyl-1-piperazinyl)carbonyloxy]-7-oxo-6,7-dihydro-5H-pyrrolo[3,4-b]pyrazine and [8-(5-chloropyridin-2-yl)-7-oxo-2,5,8-triazabicyclo[4.3.0]nona-1,3,5-trien-9-yl]-4-methyl piperazine-1-carboxylate refer to compounds represented by the following structure:

the terms Eszopiclone, LUNESTA®, (S)-(6-(5-chloro-2-pyridyl)-5-[(4-methyl-1-piperazinyl)carbonyloxy]-7-oxo-6,7-dihydro-5H-pyrrolo[3,4-b]pyrazine) and [(9S)-8-(5-chloropyridin-2-yl)-7-oxo-2,5,8-triazabicyclo[4.3.0]nona-1,3,5-trien-9-yl]-4-methyl piperazine-1-carboxylate refer to an individual enantiomer of the foregoing represented by the following structure:

The pharmaceutical compositions of the invention contemplate both the racemic mixture (also known as zopiclone), and in certain embodiments, contemplate a single enantiomer, e.g., the S-enantiomer (eszopiclone). The term "zopiclone", not otherwise modified or restricted will include not only a stereoisomeric mixture, but also individual respective stereoisomers substantially free from other stereoisomers. For example, zopiclone can encompass non-racemic mixtures of stereoisomers of the same compound (e.g., about 90, 80, 70, or 60 weight percent of one enantiomer and about 10, 20, 30, or 40 weight percent of the opposite enantiomer); and mixtures of different racemic or stereomerically pure compounds (e.g., about 90, 80, 70, or 60 weight percent of one compound and about 10, 20, 30, or 40 weight percent of another). Eszopiclone is the S-(+)-optical isomer of the compound zopiclone, which is described in U.S. Pat. Nos. 6,319,926 and 6,444,673, and in Goa and Heel (Drugs, 32:48-65 (1986)) and in U.S. Pat. Nos. 3,862,149 and 4,220,646. This isomer, which will hereinafter be referred to by its USAN-approved generic name, eszopiclone, includes the optically pure and the substantially optically pure (e.g., 90%, 95% or 99% optical purity) S-(+)-zopiclone isomer.

The compositions of the invention can be prepared by techniques known in the art. In this regard, the reader is referred to Remington's Pharmaceutical Sciences, 19th ed., Mack Publishing, Easton Pa. (1995), Chapters 92 and 93, the disclosures of which are incorporated herein by reference.

The starting materials and certain intermediates used in the synthesis of the compounds of this invention are available from commercial sources or can themselves be synthesized using reagents and techniques known in the art, including those synthesis schemes delineated herein. Racemic zopiclone is commercially available and can be made using various methods, such as those disclosed in U.S. Pat. Nos. 3,862,149 and 4,220,646. Eszopiclone can be made as described in U.S. Pat. No. 6,319,926.

Analytical methods described herein can be used for determining the presence of exposed core material in a coated solid oral dosage form. Such dosage forms comprise at least a core and a coating, and may comprise additional elements. The core material to be assayed may be an active ingredient or any other component of the core that happens to be of interest. Usually the component of most interest will be the active ingredient, but the method can be applied to other components such as binders, lubricants, disintegrating agents, etc. In many embodiments, the core will be a tablet core obtained by compression. The coating will usually be in the form of a film, which may be applied according to methods well known in the art, such as spray coating. Such techniques are described in standard textbooks, such as *Remington: The Science and Practice of Pharmacy* $19^{th}$ Ed. (1995) volume II, page 1615-1659, which is incorporated herein by reference. Depending on the function and nature of the coating, such coatings are commonly from 20 micron to 200 microns thick and comprise from 1 to 10% by weight of the total weight of the coated dosage form. Because thickness varies over a tablet (particularly if embossed), coating is usually measured by weight gain and not by thickness. Core material can arrive on the surface of a coated tablet either at the time of film coating (e.g. by dust deposition) or subsequent to coating (e.g. by film defects). The core material may also break through the film coating when the dosage is administered and the film is breached, either according to design or by film failure. In any of these circumstances, it may be desirable to monitor the presence of minute amounts (i.e. solutions <999 nM or <99 nM) of core material in "instantaneous" dissolution. As used herein instantaneous refers to times less than 60 seconds following exposure of the coated dosage form to a dissolution medium.

In an embodiment of the invention, the method comprises the following steps: (a) providing ex vivo a dissolution medium; (b) bringing the coated solid oral dosage form into contact with the dissolution medium; and (c) measuring a concentration of the core material dissolved in the dissolution medium within 60 seconds of bringing the coated solid oral dosage form into contact with the dissolution medium. Steps (a) to (c) may be repeated, whereby a plot of concentration vs time is obtained. The steps may be repeated so that multiple instances of measuring the concentration of core material occur within the 60-second time frame. The steps may also be repeated so that, although one or more measurements of concentration occur within 60 seconds, the plot of concentration vs time extends beyond the 60-second time frame. The relationship between time and concentration of the core material may be determined by (a) repeatedly bringing a single coated solid oral dosage form into contact with the dissolution medium in a single vessel at defined intervals; (b) repeatedly bringing a single coated solid oral dosage form into contact with the dissolution medium in a series of vessels at defined intervals; or (c) bringing a series of coated solid oral dosage forms into contact with the dissolution medium in a series of vessels at defined intervals. These approaches are described in further detail below.

In some embodiments, the dissolution medium is mammalian saliva or a chemically comparable solution containing amylase. The saliva may be human saliva. The saliva may be present at a concentration between 3% and 10% v/v, and the remainder of the dissolution medium may be water or an aqueous solution. In certain embodiments, the saliva or solution is present at a concentration of around 5%.

In certain aspects, the invention provides a method for treating, preventing or ameliorating various disorders using composition as described above. In one embodiment, the invention provides a method for treating and/or preventing sleep disorders.

Insomnia is characterized by difficulty in sleeping or disturbed sleep patterns. Insomnia can be of a primary nature with little apparent relationship to immediate somatic or psychic events, or secondary to some acquired pain, anxiety or depression.

In one aspect, the invention provides a method for treating or preventing a sleep disorder, including primary insomnia and sleep-awake rhythm disorders (e.g., work-shift syndrome, time-zone syndrome (jet-lag)), in a subject comprising administering to a subject in need thereof a composition as described above, such that administration of the composition treats the sleep disorder.

In another aspect, the invention provides a method for treating or preventing anxiety in a subject comprising administering to a subject in need thereof a composition as described above, such that administration of the composition treats the anxiety.

As used herein the term "anxiety" refers to an anxiety disorder. Examples of anxiety disorders treatable by the compositions and methods disclosed herein include, but are not limited to: panic attack, agoraphobia, acute stress disorder, specific phobia, panic disorder, psychoactive substance anxiety disorder, organic anxiety disorder, obsessive-compulsive anxiety disorder, posttraumatic stress disorder and generalized anxiety disorder. Anxiety as referred to herein also includes situational anxiety (e.g., as experienced by a performer prior to a performance).

In certain aspects, the racemic zopiclone can be utilized herein in the same manner as described for the S-isomer eszopiclone. However, it is recognized that use of eszopiclone can provide advantages over use of the racemic zopiclone and thereafter use of eszopiclone will be preferred for many applications.

The term "treating" or "treated" refers to administering a compound described herein to a subject with the purpose to cure, heal, alleviate, relieve, alter, remedy, ameliorate, improve, or affect a disease, the symptoms of the disease or the predisposition toward the disease.

"An effective amount" refers to an amount of a compound, which confers a therapeutic effect on the treated subject. The therapeutic effect can be objective (i.e., measurable by some test or marker) or subjective (i.e., subject gives an indication of or feels an effect). Effective doses will also vary depending on route of administration.

As used herein, and unless otherwise specified, the terms "prevent," "preventing," "prevention," and "prophylactic" refer to the prevention of the onset, recurrence or intensification of a disorder disclosed herein. The terms "prevent," "preventing," "prevention," and "prophylactic" include ameliorating and/or reducing the occurrence of symptoms of a disorder disclosed herein. The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. The reader's attention is directed to the Physician's Desk Reference, a standard text in the field, in which the term "prevent" occurs hundreds of times. No person of skill in the medical art construes the term in an absolute sense.

The coated compositions described above have exhibited improved taste characteristics relative to the uncoated compound, as demonstrated in the examples which follow.

Pharmaceutical compositions and dosage forms described herein comprise one or more active ingredients. Pharmaceutical compositions and dosage forms typically also comprise one or more pharmaceutically acceptable excipients or diluents.

The term "pharmaceutically acceptable," as used herein, refers to a component that is, within the scope of sound medical judgment, suitable for use in contact with the tissues of humans and other mammals without undue toxicity, irritation, allergic response and the like, and is commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention. Preferred pharmaceutically acceptable salts include the maleate, besylate, L-malate, mesylate, (R)-mandelate, succinate, citrate, fumarate, D-malate, D-tartrate, sulfate, L-tartrate and saccharine salts.

The invention also provides compositions comprising an effective amount of zopiclone, eszopiclone or salt thereof and an acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that can be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

Single unit dosage forms are suitable for oral administration to a patient. Examples of dosage forms include, but are not limited to: tablets, caplets, capsules, such as soft elastic gelatin capsules and cachets.

The composition, shape, and type of dosage forms will typically vary depending on their use. Ways in which specific dosage forms encompassed by this invention will vary from one another will be readily apparent to those skilled in the art. See, e.g., Remington's Pharmaceutical Sciences, op. cit.

Typical pharmaceutical compositions and dosage forms comprise one or more excipients. Suitable excipients are well known to those skilled in the art of pharmacy, and non-limiting examples of suitable excipients are provided herein. The suitability of a particular excipient can also depend on the specific active ingredients in the dosage form. For example, the decomposition of some active ingredients can be accelerated by some excipients such as lactose, or when exposed to water. This invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of zopiclone can comprise excipients that are well known in the art. In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Pharmaceutical compositions that are suitable for oral administration can be presented as discrete dosage forms, such as, but are not limited to, tablets (e.g., chewable tablets), caplets and capsules. Such dosage forms contain predetermined amounts of active ingredients, and can be prepared by methods of pharmacy well known to those skilled in the art. See generally, Remington's Pharmaceutical Sciences, 19th ed., Mack Publishing, Easton Pa. (1995).

Oral dosage forms can be prepared by combining the active ingredient(s) in an intimate admixture with at least one excipient according to conventional pharmaceutical compounding techniques. Excipients can take a wide variety of forms depending on the form of preparation desired for administration. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants can be used to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant. Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Eszopiclone, zopiclone, and the maleate, besylate, L-malate, mesylate, (R)-mandelate, succinate, citrate, fumarate, D-malate, D-tartrate, sulfate or L-tartrate salts thereof can, for example, be administered with a dosage ranging from about 0.001 to about 0.2 mg/kg of body weight, alternatively dosages between 0.1 mg and 15 mg/dose, or according to the requirements of the particular therapy. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that can be combined with the carrier materials to produce a single dosage form will vary depending upon the host treated and the particular mode of administration. In some embodiments, such preparations contain from about 20% to about 80% (w/w) active compound. In some embodiments, such preparations contain from about 0.5% to about 20% active compound. A typical preparation will contain from about 0.5% to about 5% active compound (w/w).

Lower or higher doses than those recited above can be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Like the amounts and types of excipients, the amounts and specific types of active ingredients in a dosage form can differ depending on factors such as, but not limited to, the route by which it is to be administered to patients. In human therapy, the doses depend on the effect sought and the treatment period; taken orally, they are generally between 0.5 and 15 mg per day for an adult. For many applications, unit dosages containing 0.5 mg, 1 mg, 2 mg or 3 mg of eszopiclone or its salt will be suitable. In some embodiments, the unit dosages of the eszopiclone salts can be adjusted to contain the molar equivalent of 0.5 mg, 1 mg, 2 mg or 3 mg of eszopiclone freebase.

In another aspect, the invention relates to a novel instantaneous dissolution method that is accurate, reproducible and practical for both measuring the active ingredient on the tablet surface and for evaluating the effectiveness of film coatings. This method allows for the rapid and accurate determination of the concentration of the active ingredient—or other constituent of the core in a coated oral dosage form—present in a trace level by utilizing early dissolution solutions containing aqueous human saliva solution. Additionally, the results obtained from instantaneous dissolution method correlate well with the results of human taste panel studies, and thus are useful for predicting the outcome of these studies.

A typical procedure for preparing the instantaneous dissolution solutions of coated tablets is described as follows: a tablet comprising a core and a film coating—in this case a coated eszopiclone tablet—is randomly selected, and then placed into a basket sinker (e.g., Hanson Research Part # ENMISC, BSK008-JP 8 mesh, 0.76" L×0.41" W) with long handle (made from stainless steel tubing). The basket is then immersed in dissolution diluent (e.g., 5% human saliva solution) in vial 1 for 2-5 seconds, then moved to vial 2 for 2-5 seconds dipping and so on with the same tablet. The dissolution diluents (e.g., 5% human saliva solution in water) can be prepared by mixing thoroughly about 50 mL of normal human saliva and about 950 mL of water in a suitable container. About 5 mL of the 5% human saliva solution is then pipetted into several scintillation vials (approximately 20 mL volume). This procedure has been employed with tablets coated with about 2-4% coating by weight Alternatively, the dipping experiment described above may be carried out by immersing the tablet in the basket in dissolution diluents (e.g., about 5% human saliva solution in water) in vial 1, moving the basket up and down for about 2-5 seconds at a speed of approximate 1 dip every two seconds; remove the basket from the diluent; take a sample of the diluent; re-immerse the tablet in the same vial. Continue the experiment similarly to collect samples until the tablet disintegrates or the preselected time course is completed, whichever comes first. In this embodiment, a new tablet is used in each vial. The experiment is repeated as described for additional nine or ten tablets (total of 10 tablets). The concentration of active ingredient, e.g., eszopiclone, in the sample solutions is then determined using LC/MS/MS (ESI mode, positive MRM scan type). The dissolution instantaneous profile of the tablets is constructed by plotting logarithmic concentration of eszopiclone versus time in seconds.

Another typical procedure for preparing the instantaneous dissolution solutions of coated tablets is described as follows: a number of tablets comprising a core and a film coating—in this case coated eszopiclone tablets—are transferred into basket sinkers and into a series of vials containing the dissolution diluents. The basket is then immersed in dissolution diluents (e.g., 5% human saliva solution in water) in vial 1 for 5 seconds, in vial 2 for 10 seconds, in vial 3 for 15 seconds dipping and so on with the series of tablets. The dissolution diluents (e.g., 5% human saliva solution in water) can be prepared by mixing thoroughly 50 mL of normal human saliva and 950 mL of water in a suitable container. About 5 mL of the 5% human saliva solution is then pipetted into several scintillation vials (approximately 20 mL volume). This procedure has been employed with tablets coated with 3-8% coating by weight.

In each scenario above, the concentration of core material, e.g., eszopiclone, the active ingredient in the sample solutions, is determined using LC/MS/MS (ESI mode, positive MRM scan type). The dissolution instantaneous profile of the tablets is constructed by plotting logarithmic concentration of eszopiclone versus time in seconds.

Suitable dissolution diluents include water, aqueous solutions, co-solvent solutions of water and organic solvents, human saliva solutions, solutions that mimic human saliva (particularly aqueous saline with amylase), buffer solutions, 0.01-0.1N HCl solutions and any other solutions which are able to dissolve the active ingredient and disintegrate the tablets in the instantaneous dissolution systems.

Described herein are instantaneous dissolution methods comprising a step using a LC/MS/MS technique to measure the concentration of the active ingredient in the instantaneous dissolution solution. Specifically, the LC/MS/MS procedure includes: centrifuge samples from above instantaneous dissolution solution at 6000×g for 5 minutes (if sample appears cloudy) to obtain clear solution; take out supernatant or clear solution and load into HPLC auto samplers. If the concentration of the active ingredient is above the upper calibration range (100 ng/mL), the sample solution will go through further dilution, for instance, by pipetting 100 µL of the centrifuged sample solution into 4.9 mL of sample diluents; If dilution sample is still above the calibration range, a serial dilution can be made with the dilution solution containing Internal Standard. Final diluted sample concentration should fall into the calibration range.

Suitable LC techniques include HPLC and UPLC. HPLC/MS/MS includes two parts: one part is HPLC, which is for separation the active ingredient from the sample matrix; the second part is mass spectroscopy (MS) or tandem mass spectroscopy (MS/MS) is for the detection of the active ingredient. A typical HPLC chromatographic condition is described as follows:

Guard Column. ACE guard column cartridge, 2.1 mm ID, C8 (ACE-122-0102GD)
Analytical Column: ACE C8, 5 µm, 5 cm×2.1 mm (MAC-MOD ACE-122-0502)
Mobile Phase: A: Water/0.05% Formic Acid; B: Acetonitrile
Auto Sampler Temp.: 5° C.
Column Temperature: 25° C.
Flow Rate: 0.45 mL/min
Injection Volume: 30 µL
Needle wash ACN: H2O=50:50 (v/v)
Minimum Run Time: 6.5 min

|  | Time (Minutes) | % A | % B |
|---|---|---|---|
| Gradient Program: | 0.0 | 90 | 10 |
|  | 2.0 | 5 | 95 |
|  | 3.1 | 5 | 95 |
|  | 3.2 | 90 | 10 |
|  | 6.5 | 90 | 10 |

Column Switch 100% column flow to waste for first 2.5 minutes
Make-up Solution ACN: H2O=50:50 (v/v)

Make-up flow into MS 0.45 mL/min

A typical mass spectrometer parameters and conditions are described as follows:

Scan Type: Positive MRM

Ionization Model: ESI

Gas 1: 8

Gas 2: 8

Curtain Gas: 10

Collision Gas: 8 psi

Ionspray Voltage: 5500 volt

Temperature: 450° C.

| Compound Name | Q1 | Q3 | Dwell Time | DP (v) | EP (v) | CE (v) | CXP (v) |
|---|---|---|---|---|---|---|---|
| Eszopiclone | 389.1 | 245.1 | 200 ms | 30 | 6 | 26 | 17 |
| (RS)-Zopiclone-d8 | 397.1 | 245.1 | 200 ms | 30 | 6 | 26 | 17 |

Both HPLC and MS parameters can be adjusted for optimum separation and sensitivity.

Figure 3:
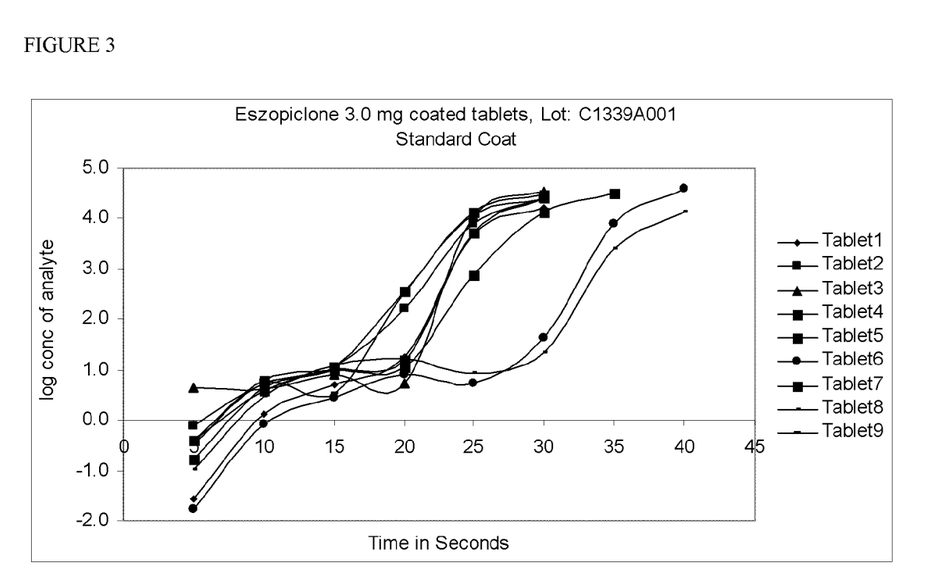
FIG. 3 depicts instantaneous dissolution profiles of 3 mg commercial Lunesta® tablets with standard coating (Opadry II, ~4.5% weight gain).
Figure 4:
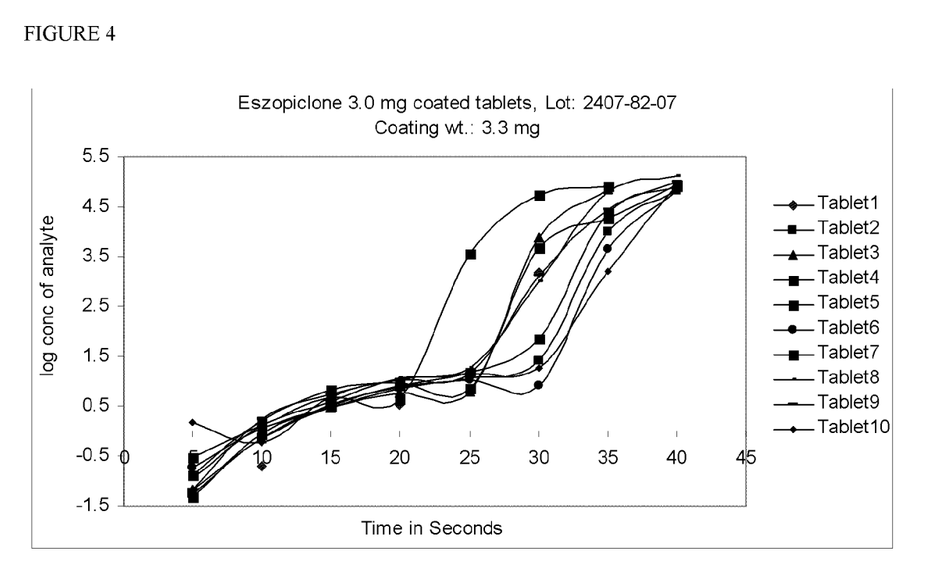
FIG. 4 depicts instantaneous dissolution profiles of 3 mg eszopiclone tablets with Opadry TM coating (about 3.3% weight gain).
Figure 5:
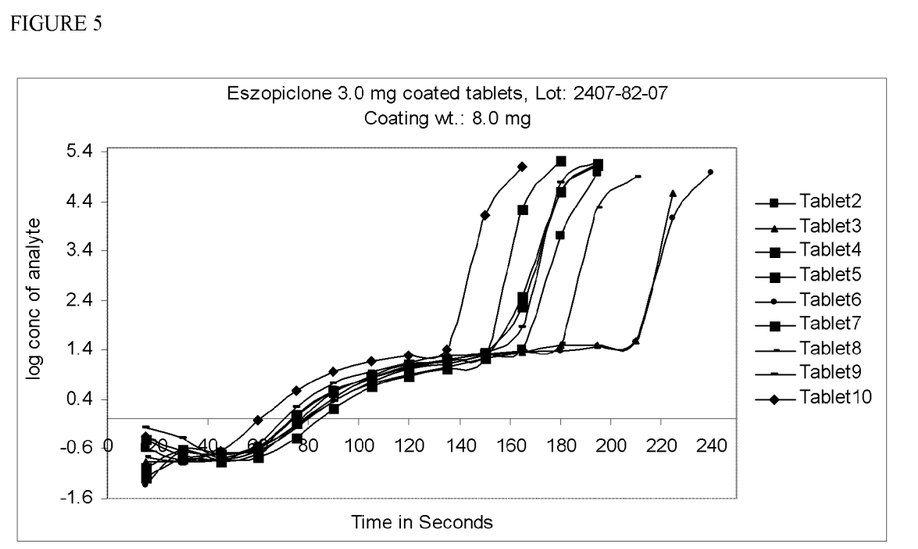
FIG. 5 depicts instantaneous dissolution profiles of 3 mg eszopiclone tablets with Opadry TM coating (about 8% weight gain).
Figure 6:
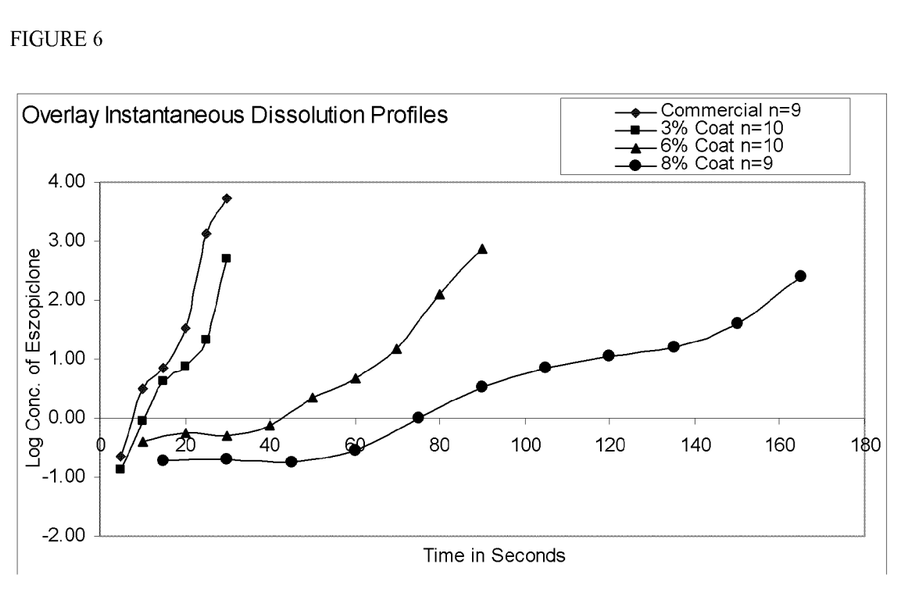
FIG. 6 depicts instantaneous dissolution profiles of 3 mg eszopiclone tablets with standard (Opadry II) coating and Opadry TM coating (about 3.3%, 6% and 8% weight gain), averaged results, n=9-10 tablets.

A typical HPLC-MS/MS analysis: Upon completion of the system suitability injections, single injections are made of each sample solution. The peak area ratio of active ingredient, e.g., eszopiclone to an internal standard (e.g., (RS)-Zopiclone-d8) is recorded. Concentration of the active ingredient, e.g., eszopiclone, in samples is calculated by extrapolating the sample/internal standard peak area ratio (y) from the calibration curve to the calculated concentration ratio on the x axis using Analyst 1.4.1 software or later version. The individual calculated concentration value and average concentration value for each time point are recorded and plotted as concentration in ng/mL as function of time in seconds for individual tablets, as shown in FIG. 3, FIG. 4 or FIG. 5. A plot of average concentration in ng/mL as a function of time in seconds for all tablets can also be made, as shown in FIG. 6.

A summary of the HPLC-MS/MS method validation results can be found in the table below:

| Validation Characteristic | Acceptance Criteria | Results |
|---|---|---|
| System Suitability | Evaluation against the criteria in the method | Method criteria was met |
| Selectivity | No interfering peak in mobile phase A, mobile phase B, dilution solution and standard diluent | Chromatographic non-interference was established |
| Accuracy and Precision (Eszopiclone; 0.1 ng/mL to 100 ng) | Accuracy: 70.0-130.0% Precision: % RSD is NMT 10.0 | Accuracy: 98.2% (93.7 to 103.2%) Precision: % RSD = 2.9 |
| Quadratic Regression | Regression: correlation coefficient is NLT 0.99 | Correlation coefficient is 1.00 |
| | Evaluate and report % dissolved results | Time seconds / Mean / % RSD<br>5 / 5.317 / 57.9<br>10 / 6.875 / 7.1<br>15 / 7.461 / 17.1<br>20 / 14.144 / 46.2<br>25 / 12.222 / 38.3<br>30 / 16.625 / 31.9<br>35 / 22.404 / 45.5<br>40 / 14.658 / 34.1<br>45 / 14.989 / 17.3<br>50 / 12.477 / 14.3 |
| Sample Solution Stability (Short Term) | Absolute % Difference in the initial peak area results for both Eszopiclone and (RS)Zopiclone-d8 and subsequent time points is NMT 20.0% Absolute % Difference in the initial peak area ratio of Eszopiclone versus (RS)Zopicolone-d8 and subsequent time points is NMT 20.0% | Sample solutions are stable for 8 hours stored at room temperature |

For comparison with the methods disclosed herein, a conventional dissolution of 3 mg eszopiclone free base tablets or 3 mg eszopiclone maleate at physiological temperature (37° C.) can be tested in dissolution media at various pH values using Hanson Research SR8-Plus Dissolution Apparatus and C-Technologies Fiber Optic UV Probes at 305 nm (excipients subtracted at 410 nm). The typical dissolution media include 0.1N HCl, pH 4.5 acetate buffers, pH 5.5 phosphate buffer, pH 6.8 phosphate buffer. A standard dissolution protocol was used. The reference standard solution (0.006 mg/mL of eszopiclone free base) is prepared by weighing a known amount (~20 mg) of the free base into a 100 mL volumetric flask. 10 mL of acetonitrile is added into the flask and sonicated until the solids dissolve completely. The solution is cooled to room temperature and made up to the 100 mL mark using dissolution medium and mixed well. From this stock solution, 3 mL is diluted to 100 mL using dissolution media. A volume of 500 mL of the dissolution medium is transferred to each of the 6 vessels in the dissolution apparatus and warmed to a temperature of 37° C. The Fiber Optic probes are immersed in each of the dissolution vessels and readings for the blank are taken for all the probes in the dissolution media. The readings for the standard are recorded for each of the individual vessels. The probes are then washed with the media and then inserted back into their respective vessels. One tablet is transferred into each vessel. The dissolution program is started immediately and readings are taken at 305 nm for 60 min (every 1 min for 20 min and then every 10 min). The conventional profiles of eszopiclone free base tablets and eszopiclone maleate tablets are shown in FIG. 1 and FIG. 2, respectively.

Figure 1:
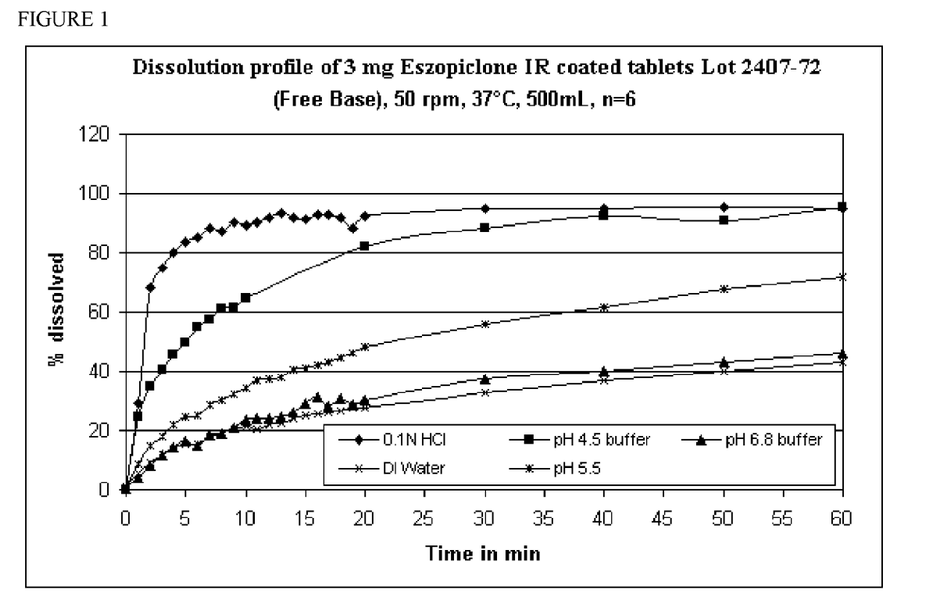
FIG. 1 depicts conventional dissolution profiles of 3 mg Lunesta® (eszopiclone free base) tablets in various dissolution media.
Figure 2:
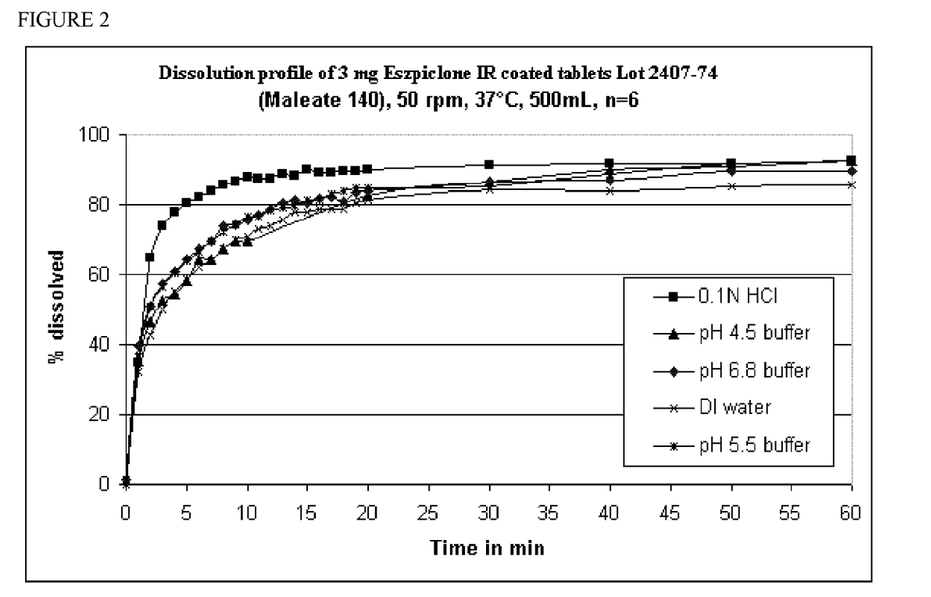
FIG. 2 depicts conventional dissolution profiles of 3 mg eszopiclone maleate tablets in various dissolution media.

FIG. 1 and FIG. 2 illustrate that the conventional dissolution method is useful to measure the dissolution profile of tablets over 45-60 minutes ranges and with a detection limit at μg/mL to mg/mL levels.

As is clear from FIG. 3-6, the instantaneous dissolution method disclosed herein is able to measure the dissolution profiles of film coated tablets over 2-30 seconds, 2-60 seconds, or 2-120 seconds ranges and with a detection limit below 999 ng/mL.

The suitable active ingredients for study by the analytical method discussed above include any pharmaceutical compounds which can be incorporated into tablets. In the examples shown, the pharmaceutical compounds have an unpleasant taste. These include eszopiclone free base, eszopiclone L-malate, eszopiclone maleate or other acid addition salts; in some cases the active ingredient is eszopiclone free base.

In a further aspect, the current invention is related to the use of the instantaneous dissolution method to predict the outcome of the clinical human taste studies or correlate the data from clinical human taste studies. The clinical human taste studies are also referred as "Lick and Roll" testing. A typical procedure of the "Lick and Roll" testing includes a 2-part study in healthy subjects who are trained sensory panelists. Six tablet coating options are blinded and tested though the study is open-label, so that the panelist know all tablets are active. Taste panelists measure the onset of bitterness of the tablet variables using the intensity scale of the Flavor Profile method of descriptive sensory analysis (Keane, 1992). Seven points are used between 0 to 3 category scale where 0 is none and 3 is strong intensity. In Part 1, the panelists evaluate the tablets by licking the tablet surface ("Lick Test") following a fixed sequence of the surface geometry, band and two faces, with six replicated evaluations at each geometry. The panelists record the number of licks required to reach a moderate intensity 2 of bitterness in every evaluation. In Part 2, the panelists evaluate the tablets by rolling tablets gently in the oral cavity ("Roll Test"), with three replicated evaluations. The panelists record the number of seconds required to reach a moderate intensity 2 of bitterness in every evaluation. The details of results are described in Example-5 of this application.

In summary, differences in tablet coating formulations and coating weight produced significant differences in bitter breakthrough, measured using a trained taste panel. Onset of bitter breakthrough can be delayed by increasing coating weight, applying a clear overcoat or modified coating formulation such as Opadry TM. The data from "Licks and Roll" method correlated well with that data from the instantaneous dissolution method. Therefore, the instantaneous dissolution method can be used to predict the human clinical taste study outcomes.

General Procedure for Coating

Preparation of Coating Suspension: Purified water is mixed with a water-soluble polymeric coating at room temperature (20° C.-25° C.) in a vortex. The ratio of solids to water in the coating suspension (solid content) is about 2% to about 20% (wt/wt), preferably about 3% to about 15% (wt/wt), and more preferably about 7% to about 13% (wt/wt). Mixing occurs at a vortex speed of 500 to 1000 rpm, for a period of time ranging from 20 to 60 minutes. A sample of the coating suspension is removed and a viscosity measurement is taken. The mixture is then de-aerated by mixing at a low speed in the vortex for at least 60 minutes.

Coating Procedure: The core solid dosage units (e.g., tablets) are loaded into an appropriate coating apparatus. Appropriate ranges for coating conditions may vary based on the coating equipment chosen; such differences may be found in the ratio of solids to water in the coating suspension preparation, target inlet temperature, spray rate, nozzle pressure, pan speed and air flow, among others. The set of ranges for various conditions utilized in the current invention depends on the size of the batch and the equipment.

The following non-limiting examples are illustrative of the invention.

Example 1

Eszopiclone 3.0 Mg Coated Tablets (Opadry® tm Coat)

18 kilograms of eszopiclone cores (3.0 mg per tablet) were coated with an Opadry coating dispersion. The Opadry dispersion of this example was made by mixing 14.58 kg of purified water with 1.62 kg of Opadry tm (07F99077, Blue), resulting in a 10% solids content, for 45 minutes in a vortex at 24° C. at 750 rpm. 100 g of the coating suspension was removed and found to have a viscosity of 336.5 cP (25° C.). The mixture was then de-aerated by mixing at a low speed for approximately one hour.

The 18 kg of core tablets (eszopiclone 3.0 mg, single dedusted cores) were loaded into a 24-inch O'Hara Labcoat Model IIX pan, which has 4 mixing baffles, a peristaltic pump, 96440-25 Masterflex tubing, 2 Spraying Systems guns (SUV113A), VF-3578-SS or VF-3578-316SS nozzles and VA113293-60-316SS or CO-VF-3578-SS air caps, for coating. The two spray guns were set to 35 g/min (70 g/min total spray rate). After 100 minutes, the desired 4.5% coating weight gain was achieved. The spraying conditions were as follows:

| Tablet Load (kg) | 18 |
| Fluid Rate (g/min) | 70 |
| Atomizing Air (psi) | 44 |
| Air Temperature (° C.) | |
| Inlet | 68 |
| Exhaust | 41 |
| Air Volume (cfm) | 300 |
| Pan Speed (rpm) | 14 |
| Coating Time (min) | 100 |
| % Weight Gain | 4.5 |

The final coated tablets were evaluated by recording the weight of a sample of 100 tablets, grinding the 100 tablets in a mortar and pestle and determining the loss on drying of the sample using a Mettler Moisture Balance (5 g sample size, 105° C., 5 mg within 50 seconds free switch off mode). The coating uniformity of the coated tablets was evaluated using Laser Induced Breakdown Spectroscopy.

Example 2

A solids content range study was conducted on a 1 kg scale. The 7% and 10% solids content samples had comparable appearances, while the 13% solids content surface was rougher. The table below illustrates viscosity results and the run time required to achieve a 4% coating weight gain.

| Solids Content (%) | Viscosity (cP) | Run Time for 4% Weight Gain (min) |
|---|---|---|
| 7 | 116 | 63 |
| 10 | 436 | 44 |
| 13 | 1180 | 32 |

Example 3

Taste Assessment

An open-label multiple-dose study of the taste profile of eszopiclone tablets was utilized to perform taste assessments. For the purpose of testing the compositions described above, the flavor profile panel consisted of four persons who have normal ability to smell and taste, have been trained in fundamental sensory principles and all aspects of the Flavor Profile technique and have considerable experience as panel members. The samples to be profiled were uniform and representative. Sample preparation and presentation were standardized and controlled.

The Flavor Profile is an art-recognized descriptive sensory analysis method used to measure the type and intensity of attributes in products and ingredients. [see Keane, P. The Flavor Profile Method. In C. Hootman (Ed.), Manual on Descriptive Analysis Testing for Sensory Evaluation ASTM Manual Series: MNL 13. Baltimore, Md. (1992).] It is based on the concept that flavor consists of identifiable taste, odor (aroma), and chemical feeling attributes, plus an underlying complex of attributes not separately identifiable. The method consists of formal procedures for describing and assessing the flavor of a product in a reproducible manner.

Tablet coatings were measured six times per surface, on both the band and the face of each tablet, by each sensory panelist. After each lick, the panelist waited several seconds to perceive any bitterness. The bitterness intensity results were obtained by using the Flavor Profile intensity scale (shown below), and the number of licks to a moderate (2) bitter intensity was recorded.

| Flavor Profile Intensity Scale |
| --- |
| 0 = None |
| 1 = Slight |
| 2 = Moderate |
| 3 = Strong |

Six separate eszopiclone tablet types varying in coating type, thickness and amount of dedusting were tested:

| Group ID | Coating | Coating Weight | Dedusting |
| --- | --- | --- | --- |
| DD (Double Dedusted) | Opadry ® II | 4.5% | Double |
| TM (Taste Mask) | Opadry ® tm | 4.5% | Standard |
| UC (Under Coated) | Opadry ® II | 2.5% | Standard |
| OC (Over Coated) | Opadry ® II | 7.5% | Double |
| CC (Clear Coat) | Opadry ® II Opadry ® Clear | 4.5% 1-2% | Double |
| ND (Not Dedusted) | Opadry ® II | 4.5% | None |

The data set was analyzed using repeated measures Analysis of Variance (ANOVA), and the band and face data were analyzed separately. A Bonferroni pairwise comparison test was used to determine significant differences between sample types. The face and band data were highly correlated (r=0.94, data not shown), and the face of the tablet took longer for the bitter taste to break through than the band.

The coating types were found to have significant differences in mean licks to bitter breakthrough, as shown in FIG. 1. In this figure, coating samples sharing the same vertical line are not statistically different.

The coating types fall into three distinct groups:

Group III: Opadry tm (4.5% coating, TM), Opadry II (7.5% coating, OC) and Opadry II plus Opadry Clear (4.5% coating and 1-2% coating, respectively; CC) required a greater number of licks to bitter breakthough than the other groups.

Group II: Opadry II double dedusted (4.5% coating, DD) and Opadry II non-dedusted (4.5% coating, ND). Dedusting showed no effect on reducing bitter breakthrough.

Group I: Opadry II (2.5% coating, UC) produced the quickest bitter breakthrough.

Tablets of other strengths can be prepared by altering the ratio of active ingredient to pharmaceutically acceptable carrier, the compression weight, or by using different punches.

Example-4

Conventional Dissolution of 3 mg Commercial Lunesta Tablets

Conventional dissolution of 3 mg eszopiclone free base tablets at physiological temperature (37° C.) was tested in dissolution media at various pH values using Hanson Research SR8-Plus Dissolution Apparatus and C-Technologies Fiber Optic UV Probes at 305 nm (excipients subtracted at 410 nm). The dissolution media used were (a) pH 1 0.1N HCl prepared by mixing 50 mL of conc HCl in 6 L of water; (b) pH 4.5 acetate buffer (20 mM) prepared by dissolving 5.88 g of sodium acetate trihydrate in 6 L of water and adjusting the pH to 4.5 with acetic acid; (c) pH 5.5 phosphate buffer (20 mM) prepared by dissolving 16.3 g of potassium dihydrogen phosphate in 6 L of water and adjusting the pH to 5.5 with NaOH; (d) pH 6.8 phosphate buffer (20 mM) prepared by dissolving 16.3 g of potassium dihydrogen phosphate in 6 L of water and adjusting the pH to 6.8 with NaOH. A standard dissolution protocol was used. The standard solution (0.006 mg/mL of eszopiclone free base) was prepared by weighing a known amount (~20 mg) of the free base into a 100 mL volumetric flask. 10 mL of acetonitrile was added into the flask and sonicated until the solids dissolved completely. The solution was cooled to room temperature and volume made up to the 100 mL mark using media and mixed well. From this stock solution, 3 mL was diluted to 100 mL using media. A volume of 500 mL of the dissolution medium is transferred to each of the 6 vessels in the dissolution apparatus and warmed to a temperature of 37° C. The Fiber Optic probes are immersed in each of the dissolution vessels and readings for the blank are taken for all the probes in the dissolution media. The readings for the standard are recorded for each of the individual vessels. The probes are then washed with the media and then inserted back into their respective vessels. One tablet was transferred into each vessel. The dissolution program was started immediately and readings were taken at 305 nm for 60 min (every 1 min for 20 min and then every 10 min). The dissolution profiles of 3 mg Commercial Lunesta Tablets in various media are shown in FIG. 1.

Example 5

Conventional Dissolution of 3 Mg Eszopiclone Maleate Tablets

Dissolution over time of 3 mg eszopiclone maleate tablets at physiological temperature (37° C.) was tested in dissolution media at various pH values using Hanson Research SR8-Plus Dissolution Apparatus and C-Technologies Fiber Optic UV Probes at 305 nm (excipients subtracted at 410 nm). The dissolution media used were (a) pH 1 0.1N HCl prepared by mixing 50 mL of conc HCl in 6 L of water; (b) pH 4.5 acetate buffer (20 mM) prepared by dissolving 5.88 g of sodium acetate trihydrate in 6 L of water and adjusting the pH to 4.5 with acetic acid; (c) pH 5.5 phosphate buffer (20 mM) prepared by dissolving 16.3 g of potassium dihydrogen phosphate in 6 L of water and adjusting the pH to 5.5 with NaOH; (d) pH 6.8 phosphate buffer (20 mM) prepared by dissolving 16.3 g of potassium dihydrogen phosphate in 6 L of water and adjusting the pH to 6.8 with NaOH. A standard dissolution protocol was used. The standard solution (0.006 mg/mL of eszopiclone free base) was prepared by weighing a known amount (~20 mg) of the free base into a 100 mL volumetric flask. About 10 mL of acetonitrile was added into the flask and sonicated until the solids dissolved completely. The solution was cooled to room temperature and made up to the 100 mL mark using media and mixed well. From this stock solution, 3 mL was diluted to 100 mL using media. A volume of 500 mL of the dissolution medium is transferred to each of the 6 vessels in the dissolution apparatus and warmed to a temperature of 37° C. The Fiber Optic probes are immersed in each of the dissolution vessels and readings for the blank are taken for all the probes in the dissolution media. The readings for the standard are recorded for each of the individual vessels. The probes are then washed with the media and then inserted back into their respective vessels. One tablet was transferred into each vessel. The dissolution program was started immediately and readings were taken at 305 nm for 60 min (every 1 min for 20 min and then every 10 min). The dissolution profiles of 3 mg eszopiclone maleate tablets are shown in FIG. 2.

Example 6

Instantaneous Dissolution of 3 mg Eszopiclone Tablets with Standard Coating (2-4.5% Weight Gains)

This procedure is applicable for preparing the instantaneous dissolution solutions of eszopiclone tablets or any tablets coated with less weight gain (2-4.5% standard coating weigh gains). The instantaneous dissolution profile of eszopiclone tablets was obtained in 5% human saliva solution in water using an HPLC/MS/MS method. The 5% human saliva solution in water was prepared by mixing thoroughly 50 mL of normal human saliva (pooled, special screening by Biochemed) and 950 mL of water (Milli-Q) in a suitable container. For the preparation of instantaneous dissolution sample solution, 5 mL (using 5 mL Eppendorf pipette) of the 5% human saliva solution was pipetted into several scintillation vials (approximately 20 mL volume). The Lunesta® tablet was placed into a basket sinker ((Hanson Research Part # ENMISC, BSK008-JP 8 mesh, 0.76" L×0.41" W) with long handle (made using stainless steel tubing). The basket was then immersed in vial 1 for 2 seconds, then moved to vial 2 for 2 seconds dipping and so on. The experiment was stopped when the tablet started disintegrating. The experiment was repeated as described for additional nine tablets (total of 10 tablets). The concentration of Eszopiclone in the samples was determined using LC/MS/MS (ESI mode, positive MRM scan type). The dissolution profile of Lunesta® tablets was obtained by plotting logarithmic concentration of eszopiclone against time in seconds, as shown in FIG. 3 or FIG. 4.

Example 7

Instantaneous Dissolution of 3 mg Eszopiclone Tablets with TM Coating (3-8% Weigh Gains)

This procedure is applicable for preparing the instantaneous dissolution solutions of Lunesta tablets or any tablets coated with higher weight gain (3-8% TM coating weigh gains). The instantaneous dissolution profile of Lunesta® (Eszopiclone) tablets was obtained in 5% human saliva solution in water using an HPLC/MS/MS method. The 5% human saliva solution in water was prepared by mixing thoroughly 50 mL of normal human saliva (pooled, special screening by Biochemed) and 950 mL of water (Milli-Q) in a suitable container. For the preparation of instantaneous dissolution sample solution, 5 mL (using 5 mL eppendorf pipette) of the 5% human saliva solution was pipetted into several scintillation vials (approximately 20 mL volume). The Lunesta® tablet was placed into a basket sinker ((Hanson Research Part # ENMISC, BSK008-JP 8 mesh, 0.76" L×0.41" W) with long handle (made using stainless steel tubing). The tablet was kept below the surface of the liquid at all times, and the basket was moved up and down for 10 seconds at a speed of approximate 1 dip every two seconds. This procedure was repeated 5-10 times using separate tablets and vials. The scintillation vials were labeled using (i.e. 10-1, 10-2 and so on up to 10-6) accordingly. The experiment was continued similarly in a fresh vial till the tablet disintegrated, in separate vials containing the dissolution diluents (e.g., 5% human saliva solution), or till the tablet disintegrates, whichever comes first, in separate vials containing the dissolution diluents (e.g., 5% human saliva solution). The concentration of active ingredient, e.g., eszopiclone, in the samples was then determined using LC/MS/MS (ESI mode, positive MRM scan type). The dissolution instantaneous profile of Lunesta® tablets was constructed by plotting logarithmic concentration of eszopiclone against time in seconds, as shown in FIG. 5 or FIG. 6.

While the foregoing examples of the instantaneous profile relate to the determination of presence of active ingredient, it will be apparent to persons of skill that the method can be applied to the determination of concentrations of other core materials as well. For example, if a tablet core contained, in addition to active ingredient, an excipient whose taste was offensive, one could use the same method to determine breakthrough of the excipient.

Example 8

Human Clinical Taste "Lick and Roll" Tests on 3 mg Eszopiclone Tablets with TM Coating Methods: This was a 2-part study in healthy subjects who were trained sensory panelists. Six tablet coating options were blinded and tested though the study was open-label that panelist knew all tablets were active. Taste panelists measured the onset of bitterness of the tablet variables using the intensity scale of the Flavor Profile method of descriptive sensory analysis (Keane, 1992). Seven points were used between 0 to 3 category scale where 0 is none and 3 is strong intensity. In Part 1, the panelists evaluated the tablets by licking the tablet surface ("Lick Test") following a fixed sequence of the surface geometry, band and two faces, with six replicated evaluations at each geometry. The panelists recorded the number of licks required to reach a moderate intensity 2 of bitterness in every evaluation. In Part 2, the panelists evaluated the tablets by rolling tablets gently in the oral cavity ("Roll Test"), with three replicated evaluations. The panelists recorded the number of seconds required to reach a moderate intensity 2 of bitterness in every evaluation.

Results and Discussions: The mean number of licks of the tablet bands ranged from 2.92 licks for Formulation UC to 8.38 licks for Formulation OC, with a 95% confidence interval of 1.63 licks. The mean lick values on the face were similar to the band with one transposition—Formulation TM requiring the most licks to bitter breakthrough, with a smaller 95% confidence interval of 0.56 licks. The mean roll values ranged from 12.4 to 23.2 seconds with Formulation UC requiring the least time and Formulation OC tablets requiring the most. The roll test data are highly correlated with the lick test data.

Those skilled in the art will recognize, or be able to ascertain using no more than routine experimentation, many equivalents of the specific embodiments of the invention described herein. Such equivalents are intended to be encompassed by the following claims.

What we claim is:

1. A pharmaceutical composition for oral administration as a solid dose comprising a therapeutically effective amount of (6-(5-chloro-2-pyridyl)-5-[(4-methyl-1-piperazinyl)carbonyloxy]-7-oxo-6,7-dihydro-5H-pyrrolo[3,4-b]pyrazine) or (S)-(6-(5-chloro-2-pyridyl)-5-[(4-methyl-1-piperazinyl)carbonyloxy]-7-oxo-6,7-dihydro-5H-pyrrolo[3,4-b]pyrazine), or a salt thereof, coated with a water-soluble polymeric coating, said polymeric coating representing 5.5% to 6.5% by weight of said composition, wherein said coating comprises at least one of hydroxypropyl methylcellulose, hydroxypropyl cellulose, methyl cellulose, hydroxyethyl cellulose or mixtures thereof.

2. The composition of claim 1, wherein said coating comprises hydroxypropyl methylcellulose.

3. The composition of claim 1, wherein said coating comprises a mixture of hydroxypropyl methylcellulose, hydroxypropyl cellulose, methyl cellulose and hydroxyethyl cellulose.

4. The composition of claim 1, wherein said coating additionally comprises a taste modifying agent.

5. The composition according to claim 1, wherein said solid dose is a tablet.

6. The composition of claim 1, wherein the composition is capable of masking the taste of (6-(5-chloro-2-pyridyl)-5-[(4-methyl-1-piperazinyl)carbonyloxy]-7-oxo-6,7-dihydro-5H-pyrrolo[3,4-b]pyrazine) or (S)-(6-(5-chloro-2-pyridyl)-5-[(4-methyl-1-piperazinyl)carbonyloxy]-7-oxo-6,7-dihydro-5H-pyrrolo[3,4-b]pyrazine), or a salt thereof, for at least 20 seconds.

* * * * *